United States Patent [19]
Jones

[11] Patent Number: 6,069,959
[45] Date of Patent: May 30, 2000

[54] ACTIVE HEADSET

[75] Inventor: Owen Jones, Ipswich, United Kingdom

[73] Assignee: Noise Cancellation Technologies, Inc., Linthicum, Md.

[21] Appl. No.: 08/846,443

[22] Filed: Apr. 30, 1997

[51] Int. Cl.[7] .................................................. A61F 11/06
[52] U.S. Cl. ...................... 381/71.6; 330/262; 381/120
[58] Field of Search ........................... 381/71.13, 71.6, 381/74, 71.1, 120; 330/262

[56] References Cited

U.S. PATENT DOCUMENTS

| | | | |
|---|---|---|---|
| 4,455,675 | 6/1984 | Bose et al. ................................... | 381/74 |
| 4,953,217 | 8/1990 | Twiney et al. .......................... | 381/71.6 |
| 5,732,143 | 3/1998 | Andrea et al. ........................ | 381/71.13 |
| 5,774,565 | 6/1998 | Bennings et al. ....................... | 381/71.6 |

*Primary Examiner*—Ping Lee
*Attorney, Agent, or Firm*—Renee Michelle Larson

[57] ABSTRACT

An active headset providing for reduction of external noise over a given frequency range by means of a microphone which generates an external noise representative signal processed and fed to a loudspeaker to produce an external noise cancellation signal spectrum, wherein a bridge amplifier circuit is interposed between the microphone and the loudspeaker and the gain of the bridge amplifier for peak amplitude of the noise cancellation signal is user adjustable without substantially reducing the breadth of the given frequency range over which noise reduction is effective.

15 Claims, 5 Drawing Sheets

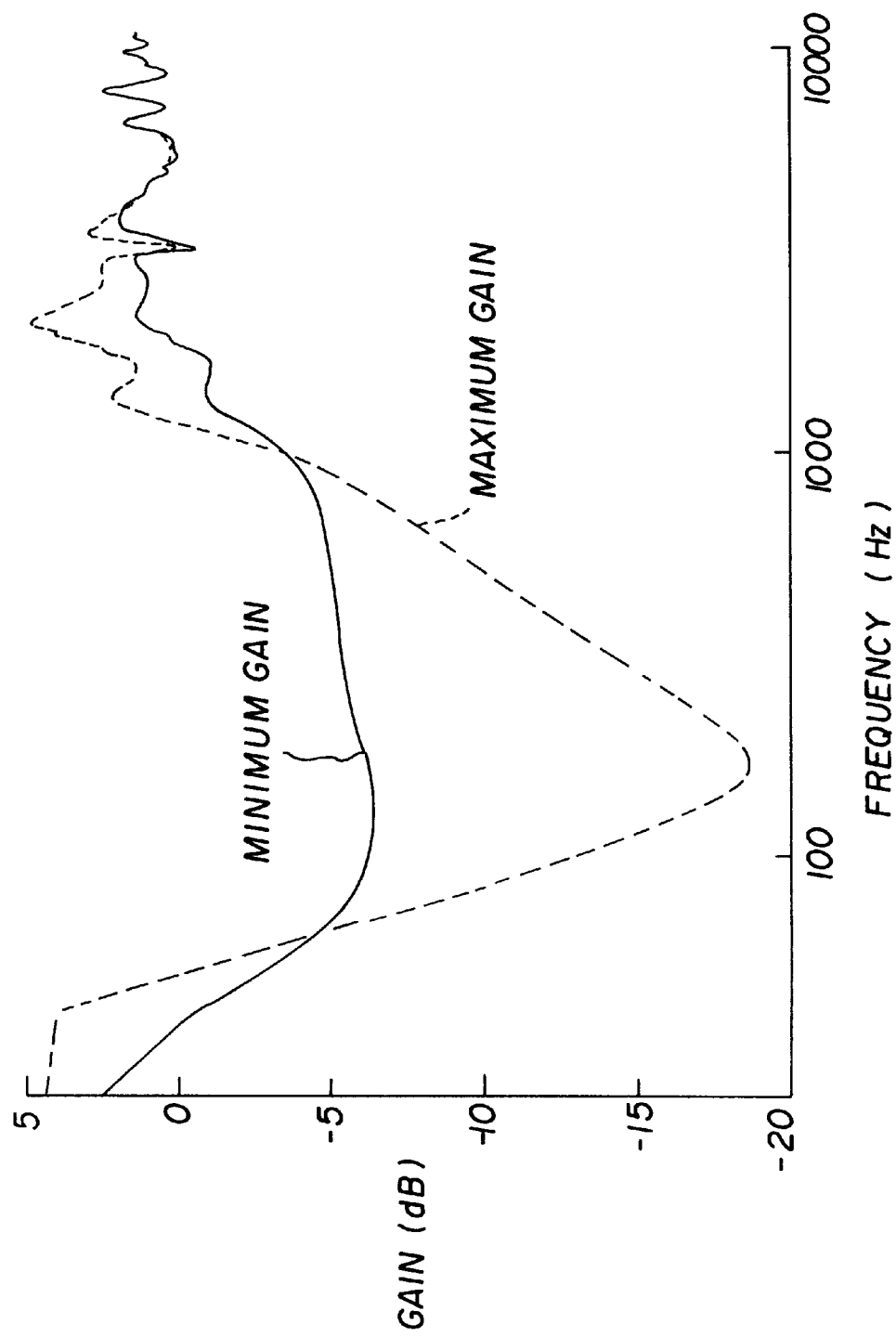

ACTIVE HEADSET

BACKGROUND OF THE INVENTION

1. Field of the Invention

This invention relates to an active headset for reducing the amount of external noise reaching the ear under noisy conditions, for example in an aircraft or other vehicle.

2. Background of the Invention

Such active headsets are well known and include a microphone in each earpiece for generating a signal representative of detected external noise and an earphone in each earpiece which propagates a noise cancellation signal generated by processing of the external noise representative signal produced by the microphone.

It is generally accepted that, due to time delay problems, only a given range of lower frequencies present in the external noise can be canceled.

Nevertheless, some users feel discomfort when wearing active headsets providing noise cancellation over the given frequency range, as they experience a feeling of pressure within the ears.

From U.S. Pat. No. 5,138,664 is known an active headset which includes a conventional variable gain amplifier interposed between the microphone and the loudspeaker, whereby the user can vary the peak amplitude of the noise cancellation signal. In the arrangement disclosed in this patent, however, variation of the peak amplitude of the noise cancellation spectrum is accompanied by marked variation in the total range of frequencies over which noise reduction is effective.

There is thus an unmet need in the art to provide an active headset that can cancel external noise in both the higher and lower frequency range while reducing a users feeling of pressure within the ears.

SUMMARY OF THE INVENTION

It is an object of the invention to provide an active headset that can cancel external noise in both the higher and lower frequency ranges.

It is another object of the invention to provide an active headset that reduces the subjective pressure within the ears felt by a user.

Therefore, according to the present invention, there is provided an active headset incorporating means for reducing the amount of external noise reaching the ear by generation of a noise cancellation signal extending over a given frequency range, wherein means are provided for use by the user for adjustment of gain at the peak amplitude of the noise cancellation spectrum substantially without reducing the breadth of the given frequency range over which noise reduction is effective.

In a preferred arrangement, the gain of the noise cancellation signal is determined by a bridge amplifier circuit in which the summation node is provided within a resistive/capacitive coupling providing feedback to the feedback input of the operational amplifier in the non-inverting part of the bridge amplifier circuit, and the peak amplitude of the noise cancellation signal is adjustable by means of a variable component in the said resistive/capacitive coupling providing feedback, such as a variable resistance or switchable capacitor.

BRIEF DESCRIPTION OF THE DRAWINGS

The novel features believed characteristic of the invention are set forth in the claims. The invention itself, however, as well as a preferred mode of use, and further objects and advantages thereof, will be understood by reference to the following detailed description of an illustrative embodiment when read in conjunction with the accompanying drawing, wherein:

FIG. 5 is a graph showing characteristic curves applicable to the circuit of FIG. 4.

DESCRIPTION OF THE INVENTION

Figure 1:
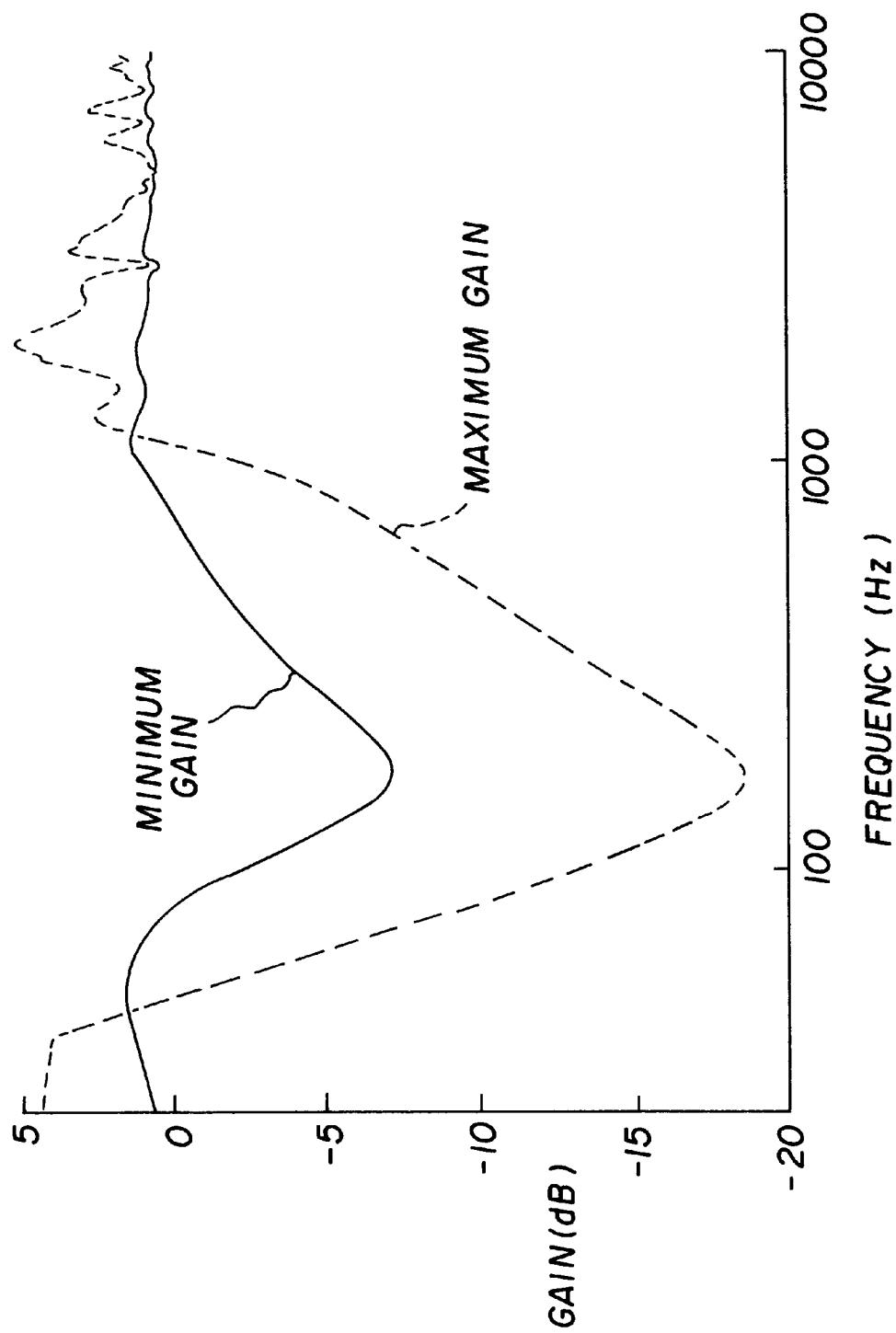
FIG. 1 is a graph showing characteristic curves applicable to the use of a conventional operational amplifier configuration for variation of the gain of the noise cancellation signal.

As can be seen from FIG. 1, the disadvantage of use of a conventional variable gain amplifier interposed between the microphone and the earphone of an active headset, wherein amplification is changed by alteration of the bias voltage, is that when the peak amplitude of the noise cancellation spectrum is changed from maximum to minimum, there is a very substantial reduction in the range of frequencies over which noise reduction is achieved.

Figure 2:
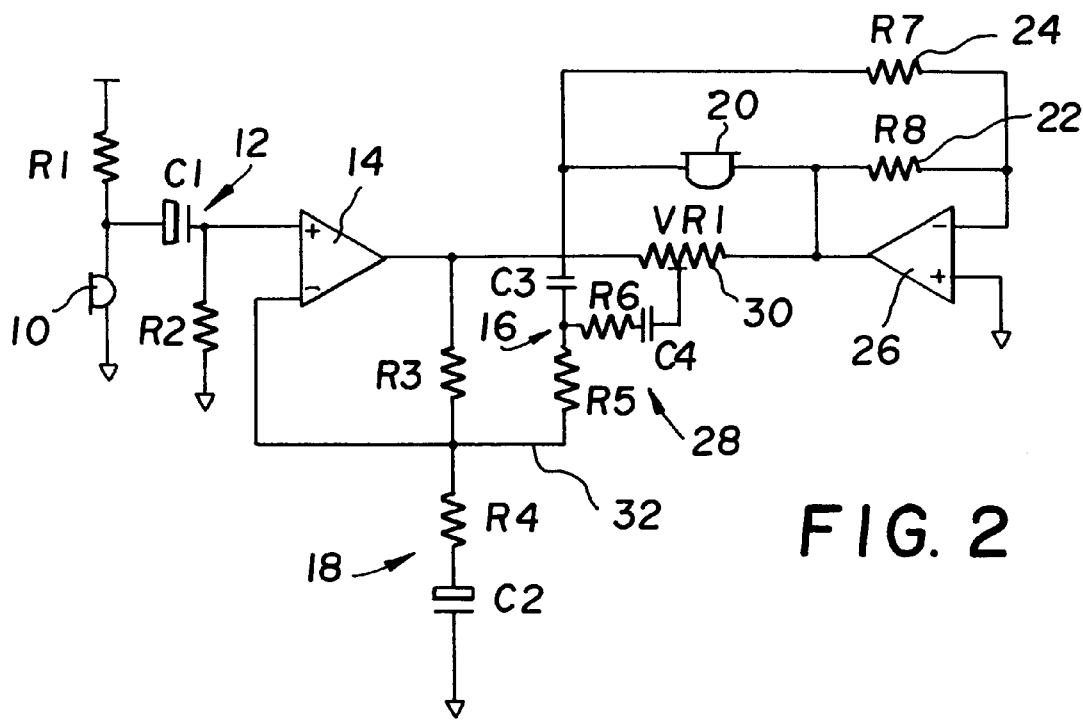
FIG. 2 is a circuit diagram for one embodiment of active headset in accordance with the present invention.

FIG. 2 shows a bridge amplifier circuit used in one embodiment of the present invention. Constructionally, the circuit can be briefly described as follows.

The microphone 10 is connected, via a capacitive-resistive coupling 12, to the non-inverting input of an operational amplifier 14 in the non-inverting part of the bridge circuit.

The output of the operational amplifier 14 is connected, past a ground resistive/capacitive line 18, to a summation node 16 at a junction within a capacitive/resistive combination 28. From the summation node 16, a resistive path 32 leads back to the inverting input of the operational amplifier 14.

The loudspeaker 20 is connected between the outputs of the amplifiers 14 and 26 with resistors 22 and 24 connecting between the output of the amplifier 14 and inverting input of amplifier 26 and output of 26 and inverting input of 26 respectively, to form the inverting part of the bridge amplifier. The non-inverting input of amplifier 26 connects to ground and the output connects back to the summation node via the resistive/capacitive combination 28, which includes a variable resistance 30.

The operation of the circuit is as follows. The circuit of FIG. 2 can be separated into three functional parts. The first is built up around the components $R_1$, $C_1$, $R_2$, $R_3$, $R_4$, $C_2$, $R_5$, $C_3$ and the operational amplifier 14. These components act as an amplifier circuit with a shelf in the frequency response whereby $R_5$ and $C_3$ act to reduce the gain of the amplifier at high frequencies. This is part of the equalization necessary for the active headset system in which the amplifier circuit is incorporated, and the circuitry for this purpose is well understood in the art.

The second part of the circuit of FIG. 2 is the bridge amplifier circuit constructed by the components $R_7$, $R_8$ and the second operational amplifier 26. This operational amplifier 26 is configured as a unity gain inverting amplifier circuit, the input of which is taken from the output of the first amplifier circuit. The output of the second amplifier circuit is thus identical to that of the first but inverted in phase so that the output voltage swing across the earphone is double that of a single amplifier for the same supply voltage. Such practice is known from studio power amplifiers.

The third part of the circuitry, provided for the purposes of the present invention, is the positive feedback path formed by $VR_1$, $R_6$ and $C_4$. This is responsible for the particular frequency response changes produced by adjusting $VR_1$ (30). The action of this network is to peak up the gain of the circuit in a band typically centered around 200 Hz when $VR_1$ (30) is set to give maximum positive feedback with its adjustment control set to one extreme, and to damp down the gain by producing negative feedback when the control is set to the opposite extreme. With the control set to a mid position there is no feedback at all through this network and the gain of the circuit is unaltered.

The particular frequency response characteristics that the bridge amplifier circuit produces are important from the point of view of the cancellation produced when the circuit is connected into a virtual earth, active headset system. The characteristic is tailored so that the cancellation is affected most around the middle of the band of cancellation produced at the ear, so that the stability of the noise canceling headset is not compromised by the adjustment of $VR_1$ (30). This ensures that the subjective pressure effect felt by the user on the ears with such an active headset is lessened by reducing the cancellation without drastically affecting the frequency extremes, as would normally be the case if the overall gain of the system was reduced, for example by reducing the value of $R_1$.

If the positive feedback was simply to be applied by means of a feedback resistor then the effect upon the frequency response would be little better than that produced by altering $R_1$. To make the response frequency dependent the positive feedback has itself been made to diminish at both high and low frequencies. At low frequencies the feedback is lessened by the inclusion of $C_4$, the impedance of which rises as frequency falls. The reduction of positive feedback at high frequencies is achieved without the need for additional components by judiciously choosing the point at which to inject the feedback into the first amplifier circuit. It would normally be the case that any additional feedback signals would be injected directly into the inverting or non-inverting nodes of the operational amplifier 14, but in the circuit of FIG. 2 the positive feedback is connected into the junction of $R_5$ and $C_3$. Without the positive feedback, the order of the series connection of $R_5$ and $C_3$ would be unimportant, but with the circuit arrangement shown in FIG. 2 it is arranged that $C_3$ is connected to the output and $R_5$ to the inverting input of the operational amplifier 14. This ensures that as the impedance of $C_3$ falls with increasing frequency, thereby reducing the gain of the first part of the circuit, as described above, it also reduces the effectiveness of the positive feedback. $C_3$ thus performs two tasks at once and reduces the total number of components necessary.

Figure 4:
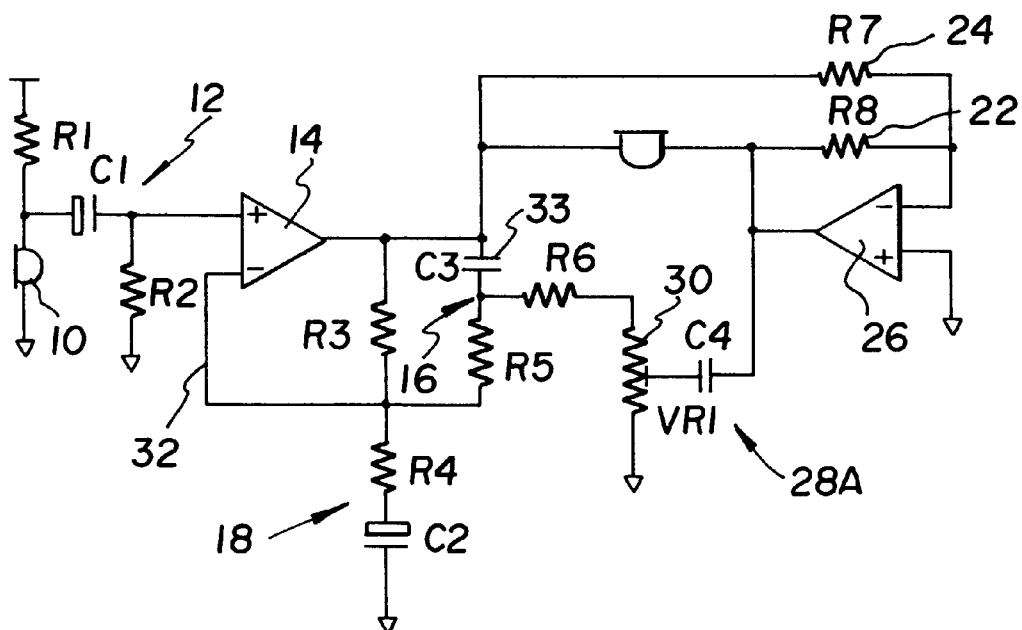
FIG. 4 is a circuit diagram for an alternative embodiment of active headset in accordance with the present invention.

The circuit of FIG. 4 is similar, but the resistive/capacitive combination 28A, analogous to the combination 28 of FIG. 2, is differently arranged, primarily for bandwidth control instead of direct gain control.

Thus, the operation of the circuit of FIG. 4 is as follows. Broadly, the circuit of FIG. 4 alters the frequency response in a different manner. Although the circuit of FIG. 2 does reduce the pressure effect on the ears as $VR_1$ (30) is adjusted, it is still not as effective as it might be. This arises because the subjective pressure effect felt by the active headset user has been found to be more dependent upon the amount of high frequency cancellation than the low. As mentioned previously, simply reducing the overall circuit gain removes too much cancellation at the frequency extremes. The circuit of FIG. 4, on the other hand, has the characteristic that the cancellation response shape has a variable slope above 200 Hz with a pivot point centered on approximately 1.5 kHz. This characteristic has been found to be more effective in reducing the pressure effect while still maintaining an effective amount of active noise cancellation.

The operation of the circuit of FIG. 4 is similar to that of FIG. 2 except in the manner in which the positive feedback is derived. The circuit values $R_3$, $R_5$ and $C_3$ are altered from those of FIG. 2 so that only positive feedback is required. $VR_1$ (30) is this time a much higher value than in FIG. 2 and is connected so that instead of acting simply as a voltage divider to the output voltage, it also acts as a variable resistance element. In this way, as its control element is moved towards the ground end of the variable resistance, the amount of positive feedback is decreased, but at the same time the constant formed by $C_4$, $VR_1$ and $R_6$ is increased, thus moving the frequency at which the peak in the gain of the circuit occurs downwards. This ensures that the low frequency gain is reduced at a lesser rate than the high frequency gain as $VR_1$ (30) is adjusted, giving rise to the required variable slope characteristic.

Broadly, the effect of the capacitive/resistive combination 28 or 28A is to make the cancellation effect less frequency dependent, at the lower amplitudes obtainable by use of the variable resistance 30, over the given frequency range for which noise reduction is required.

Figure 3:
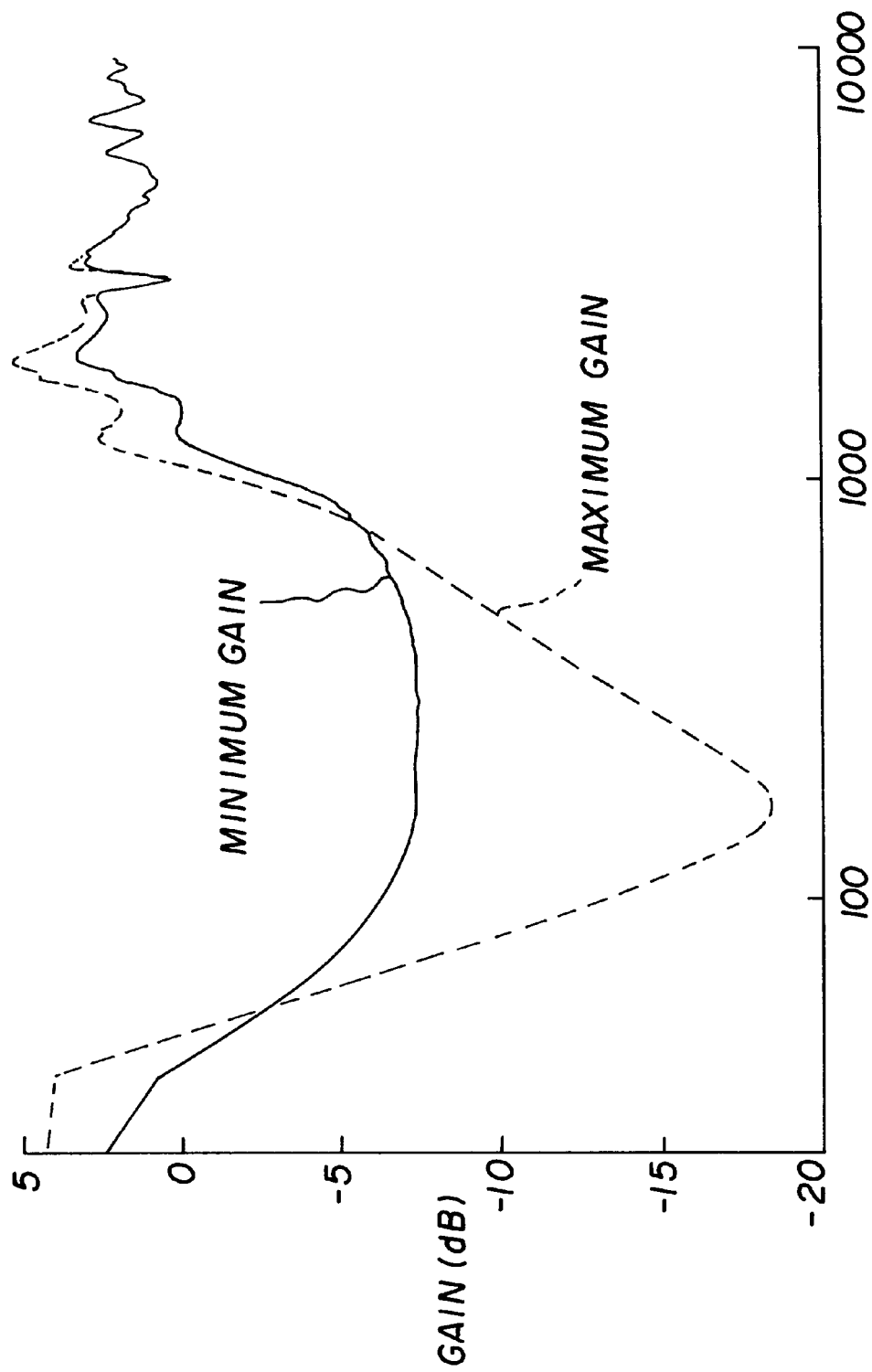
FIG. 3 is a graph showing characteristic curves applicable to the circuit of FIG. 2.

This can be seen from the graphs of FIGS. 3 and 5. The user is now able to reduce the peak amplitude of the noise cancellation spectrum, to the extent necessary to ease discomfort, substantially without reducing the range of frequencies over which noise reduction is achieved. The particular advantage of the circuit of FIG. 4 can be clearly seen, wherein the variable resistance 30 has a greater effect at the higher frequencies of the range being handled.

Figure 6:
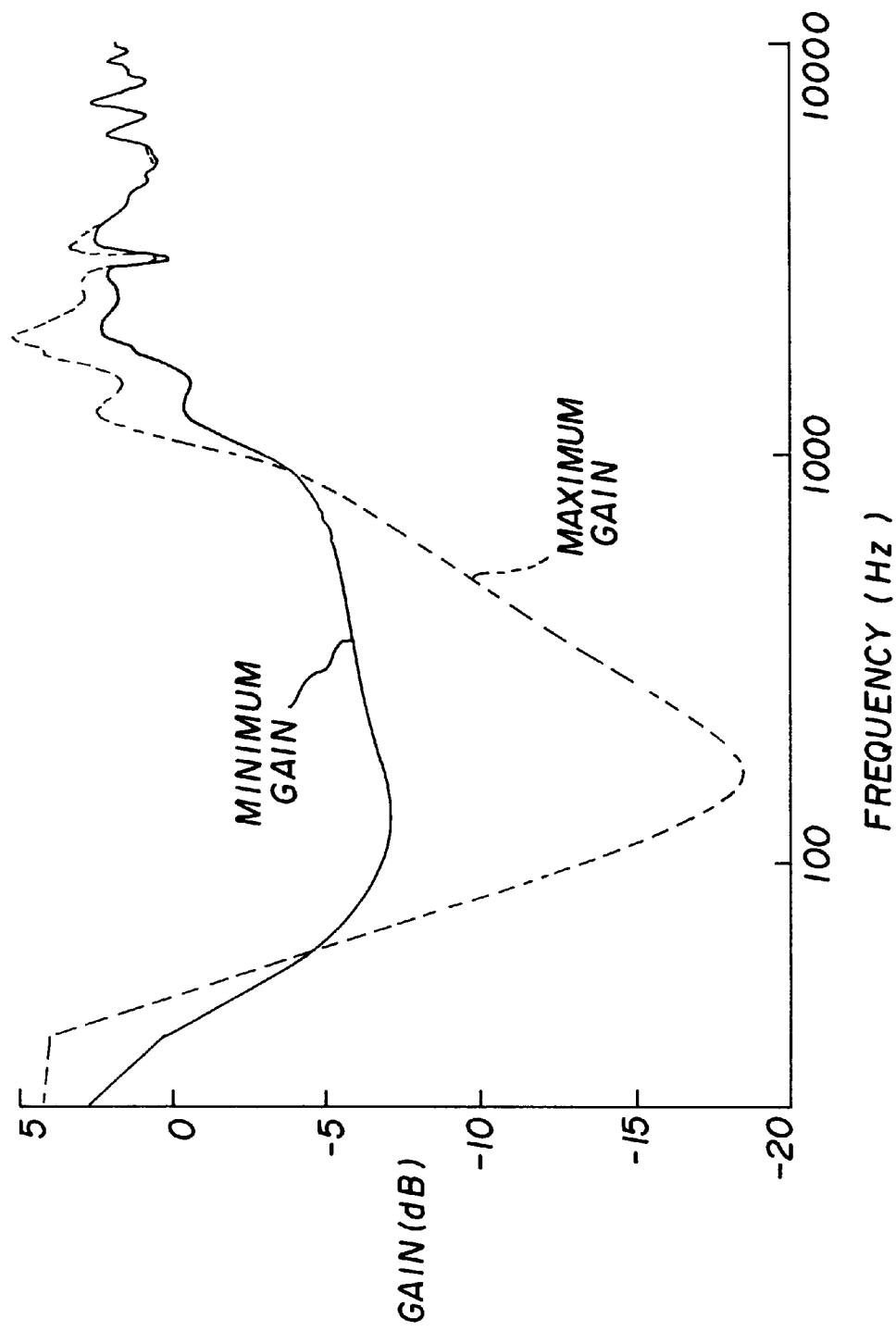
FIG. 6 is a graph showing characteristic curves applicable to a modification of FIG. 2 or FIG. 4 employing switchable capacitors instead of variable resistance.

As shown by the graph of FIG. 6, when compared with the graph of FIG. 5, a generally similar result can be achieved by replacing the variable resistance 30 with a fixed resistance and providing switchable capacitors of differing values in place of the capacitor 33 in the coupling 28A.

While the invention has been particularly shown and described with reference to a preferred embodiment, it will be understood by those skilled in the art that various changes in form and detail may be made therein without departing from the spirit and scope of the invention.

What is claimed is:

1. An active headset incorporating noise cancellation circuitry for reducing the amount of external noise reaching a user's ear by generation of a noise cancellation signal spectrum extending over a given frequency range, comprising:

an adjustment element that adjusts a noise cancellation gain/frequency response of the noise cancellation circuitry without substantially reducing the breadth of the given frequency range over which noise reduction of external noise reaching the user's ear is effective, wherein the adjustment element further comprises:
a bridge amplifier circuit having a resistive-capacitive coupling, the resistive-capacitive coupling having a summation node providing a high frequency shelf for an operational amplifier in a non-inverting amplifier stage of the bridge amplifier circuit.

2. An active headset according to claim 1, wherein, at a position of adjustment producing a minimum peak gain, the noise cancellation gain/frequency response of the noise cancellation circuitry is substantially flat over a substantial portion of the given frequency range.

3. An active headset according to claim 1, wherein the adjustment element accomplishes a continuous range of adjustment of the noise cancellation gain/frequency response of the noise cancellation circuitry.

4. An active headset according to claim 3, wherein the continuous range of adjustment is achieved by a variable resistance.

5. An active headset according to claim 3, wherein the continuous range of adjustment is achieved by a plurality of switchable capacitors of the noise cancellation circuitry.

6. An active headset incorporating noise cancellation circuitry for reducing the amount of external noise reaching a user's ear by generation of a noise cancellation signal spectrum extending over a given frequency range, comprising:

an adjustment element that adjusts a noise cancellation gain/frequency response of the noise cancellation circuitry without substantially reducing the breadth of the given frequency range over which noise reduction of external noise reaching the user's ear is effective, wherein the adjustment element further comprises:
an amplifier having a non-inverting amplifier stage and an inverting amplifier stage; and
a resistive-capacitive coupling having a summation node providing a high frequency shelf for the amplifier in the inverting amplifier stage.

7. An active headset according to claim 6, wherein, at a position of adjustment producing a minimum peak gain, the noise cancellation gain/frequency response of the noise cancellation circuitry is substantially flat over a substantial portion of the given frequency range.

8. An active headset according to claim 6, wherein the adjustment element accomplishes a continuous range of adjustment of the noise cancellation gain/frequency response of the noise cancellation circuitry.

9. An active headset according to claim 8, wherein the continuous range of adjustment is achieved by a variable resistance.

10. An active headset according to claim 9, wherein the continuous range of adjustment is achieved by a plurality of switchable capacitors of the noise cancellation circuitry.

11. An active headset incorporating noise cancellation circuitry for reducing the amount of external noise reaching a user's ear by generation of a noise cancellation signal spectrum extending over a given frequency range, comprising:

an operational amplifier having a non-inverting amplifier stage and an inverting amplifier stage;
a resistive-capacitive coupling providing a high frequency shelf for the operational amplifier in the inverting amplifier stage, the resistive-capacitive coupling having a summation node; and
a means for adjustment of gain comprising a variable component of the resistive-capacitive coupling.

12. An active headset according to claim 11, wherein the means for adjustment of gain further comprises:
a variable resistance having an adjustable tapping, the variable resistance being capacitively connected between the summation node and the operational amplifier in the inverting amplifier stage; and
the adjustable tapping of the variable resistance being connected by the resistive-capacitive coupling to the summation node.

13. An active headset according to claim 8, wherein the means for adjustment of gain further comprises:
a variable resistance having an adjustable tapping, the variable resistance being connected to the summation node by a resistive coupling; and
the adjustable tapping of the variable resistance being capacitively coupled to the operational amplifier in the inverting amplifier stage.

14. An active headset according to claim 11, wherein the means for adjustment of gain further comprises a plurality of switchable capacitors connected between the summation node and the output of the operational amplifier in the inverting amplifier stage.

15. An active headset according to claim 8, wherein the non-inverting amplifier stage and the inverting amplifier stage are constituted by a bridge amplifier.

* * * * *